United States Patent
Hunziker et al.

(10) Patent No.: US 6,548,058 B1
(45) Date of Patent: *Apr. 15, 2003

(54) KERATINOCYTE CULTURE AND USES THEREOF

(75) Inventors: Thomas Hunziker, Oberhofen (CH); Alain Limat, Tavel (CH)

(73) Assignee: Epitech, S.A., Tortola (VG)

( * ) Notice: Subject to any disclaimer, the term of this patent is extended or adjusted under 35 U.S.C. 154(b) by 0 days.

This patent is subject to a terminal disclaimer.

(21) Appl. No.: 09/358,181

(22) Filed: Jul. 20, 1999

(51) Int. Cl.$^7$ ................................................ C12N 5/00
(52) U.S. Cl. ..................................................... 424/93.7
(58) Field of Search ....................................... 424/93.7

(56) References Cited

U.S. PATENT DOCUMENTS

| | | | | |
|---|---|---|---|---|
| 5,580,781 A | | 12/1996 | Naughton et al. | 435/240 |
| 5,968,546 A | * | 10/1999 | Bauer et al. | 424/444 |

FOREIGN PATENT DOCUMENTS

| | | |
|---|---|---|
| DE | 196 51 992 A | 6/1998 |
| WO | WO 93/08776 | 5/1993 |

OTHER PUBLICATIONS

Leonoir–Vitale et al., Archives of Dermatological Research 285 (4):197–204 (1993).
Limat et al., J. Investigative Dermatology 107 (1):128–135 (1996).
Eisen et al., Responses of the Superficial Portion of the Human Pilosebaceous Apparatus to Controlled Injury, *The Journal of Investigative Dermatology*, 15:145–155 (1955).
Montagna et al., The Structure and Function of Skin 172–258, (Academic Press New York, NY 1974).
Coulombe et al., Expression of Keratin K14 in the Epidermis and Hair Follicle: Insights into Complex Programs of Differentiation, *The Journal of Cell Biology*, 109:2295–2312 (1989).
Limat et al., Restoration of the Epidermal Phenotype by Follicular Outer Root Sheath Cells in Recombinant Culture with Dermal Fibroblasts, *Experimental Cell Research*, 194: 218–227 (1991).
Limat et al., Outer root sheath (ORS) cells organize into epidermoid cyst–like spheroids when cultured inside Matrigel: a light–microscopic and immunohistological comparison between human ORS cells and interfollicular keratinocytes, *Cell & Tissue Research*, 275:169–176 (1994).
Cotsarelis et al., Label–Retaining Cells Reside in the Bulge Area of Pilosebaceous Unit: Implications for Follicular Stem Cells, Hair Cycle, and Skin Carcinogenesis, *Cell*, 61:1329–1337 (1990).
Kobayashi et al., Segregation of keratinocyte colony–forming cells in the bulge of the rat vibrissa, *Proc Natl Acad Sci USA*, 90:7391–7395 (1993).
Yang et al., Upper Human Hair Follicle Contains a Subpopulation of Keratinocytes with Superior In Vitro Proliferative Potential, *J Invest Dermatol* 101(5):652–659 (1993).
Rochat, et al., Location of Stem Cells of Human Hair Follicles by Clonal Analysis, *Cell* 76:1063–1073 (1994).
Moll et al., Proliferative Potential of Different Keratinocytes of Plucked Human Hair Follicles, *J Invest Dermatol*, 105:14–21 (1995).
Weterings et al., A method for culturing human hair follicle cells, *British Journal of Dermatology*, 104:1–5 (1981).
Limat and Noser, Serial Cultivation of Single Keratinocytes from the Outer Root Sheath of Human Scalp Hair Follicles, *J Invest Dermatol*, 87:485–488 (1986).
Imcke et al., Growth of human hair follicle keratinocytes in vitro, *J Am Acad Dermatol*, 17:779–786 (1983).
Limat et al., Post–Mitotic Human Dermal Fibroblasts Efficiently Support the Growth of Human Follicular Keratinocytes, *J Invest Dermatol*, 92:758–762 (1989).
Stark et al., Keratins of the human hair follicle: "Hyperproliferative" keratins consistently expressed in outer root sheath cells in vivo and in vitro, *Differentiation*, 35:236–248 (1987).
Limat et al., Experimental Modulation of the Differentiated Phenotype of Keratinocytes from Epidermis and Hair Follicle Outer Root Sheath and Matrix Cells, *Annals of The New York Academy of Sciences*, 642:125–147 (1991).
Lenoir et al., Outer Root Sheath Cells of Human Hair Follicle Are Able to Regenerate a Fully Differentiated Epidermis in Vitro, *Developmental Biology*, 130:610–620 (1988).
Limat et al., Formation of a Regular Neo–Epidermis By Cultured Human Outer Root Sheath Cells Grafted on Nude Mice, *Transplantation*, 59(7):1032–1038 (1995).
O'Connor et al., Grafting of Burns with Cultured Epithelium Prepared from Autologous Epidermal Cells, *The Lancet*, 1:75–78 (1981).
Compton et al., Skin Regenerated from Cultured Epithelial Autografts on Full–Thickness Burn Wounds from 6 Days to 5 Years after Grafting, *Laboratory Investigation*, 60(5):600–612 (1989).
Carter et al., Treatment of junctional epidermolysis bullosa with epidermal autografts, *J Am Acad Dermatol*, 17:246–250 (1987).

(List continued on next page.)

Primary Examiner—Jean C. Witz
(74) Attorney, Agent, or Firm—Mintz, Levin, Cohn, Ferris, Glovsky and Popeo, P.C.; Ivor R. Elrifi, Esq.; Christina V. Karnakis, Esq.

(57) ABSTRACT

The present invention relates to the treatment of skin defects by organotypically-cultured autologous keratinocytes isolated from the outer root sheath of anagenic or growing hair. Methods for primary, as well as subsequent organotypic cultures (i.e., epidermal equivalents) in fully-defined media supplemented by autologous human serum and substances isolated from blood components, with minimal allogeneic biological supplements, are disclosed herein. Techniques to prepare epidermal equivalents for transplantation by use of a biocompatible glue are also disclosed herein.

22 Claims, No Drawings

OTHER PUBLICATIONS

Dean et al., The Use of Cultured Epithelial Autograft in a Patient with Idiopathic Pyoderma Gangrenosum, *Ann Plast Surg*, 26:194–195 (1991).

Limova and Mauro, Treatment of Pyoderma Gangrenosum with Cultured Keratinocyte Autografts, *J Dermatol Surg Oncol*, 20:833–836 (1994).

Gallico et al., Cultured Epithelial Autografts for Giant Congenital Nevi, *Plastic and Reconstructive Surgery*, 84:1–9 (1989).

Higgins et al., Use of two stage keratinocyte–dermal grafting to treat the separation site in conjoined twins, *Journal of the Royal Society of Medicine*, 87:108–109 (1994).

Brysk et al., 25 J. Am. Acad. Dermatol. 238–244 (1991).
Fabre, 29 Immunol. Lett. 161–166 (1991).
Harris et al., 18 Clin. Exp. Dermatol. 417–420 (1993).
Hetton et al., 14 J. Am. Acad. Dermatol. 399–405 (1986).
Hunyadi et al., 14 J. Dermatol. Surg. Oncol. 75–78 (1988).
Johnson et al., 11 J. Burn Care Rehab. 504–509 (1990).
Leigh et al., 117 Brit. J. Dermatol. 591–597 (1987).
Leigh et al., 11 Clin. Exp. Dermatol. 650–652 (1986).
Mol et al., J. Am. Acad. Dermatol. 77–82 (1991).
Moll et al., 46 Hautarzt 548–552 (1995).
Phillips et al., 21 J. Am. Acad. Dermatol. 191–199 (1989).

* cited by examiner

KERATINOCYTE CULTURE AND USES THEREOF

FIELD OF THE INVENTION

The present invention relates to the field of cell culture of human keratinocyte precursor and dermal fibroblast cells. In addition, the present invention also relates to the use of cultured keratinocyte precursor cells in the repair of skin defects by skin grafting procedures.

BACKGROUND OF THE INVENTION

The healing of skin defects progresses through three general phases: (i) inflammation, (ii) wound cell migration and mitosis, and (iii) extracellular matrix production and remodeling. The ordered sequence of these events is thought to be orchestrated by interactions among cells, growth factors, and extracellular matrix proteins. A crucial step of skin wound healing is epidermal regeneration (i.e., re-epithelialization). Besides interfollicular epidermal keratinocytes from the wound edges, the outer root sheath (ORS) cells from residual hair follicles also contribute to this process. See e.g., Eisen, et al., 1955. *J. Invest. Dermatol.* 15: 145–155. The ORS of hair follicles is comprised largely of undifferentiated keratinocytes that encompass the cylindrical structures of the hardened inner root sheath and the hair shaft. See e.g., Montagna and Parakkal, 1974. pp. 172–258. In: *The Structure and Function of Skin* (Academic Press New York, N.Y. Recent literature has also indicated that ORS cells are at a lower level of commitment to differentiation than the basal interfollicular keratinocytes (see e.g., Coulombe, et al., 1989. *J Cell Biol.* 109: 2295–2312; Limat, et al., 1991. *Exp. Cell Res.* 194: 218–227; Limat, et al., 1994. *Cell Tissue Res.* 275: 169–176 1994), and label-retaining cells have been detected in the animal as well as the human ORS region near the bulge area which possibly represent stem cells for skin epithelial tissues. See e.g., Cotsarelis, et al., 1990. *Cell* 61: 1329–1337; Kobayashi, et al., 1993. *Proc. Natl. Acad. Sci.* USA 90: 7391–7395; Yang, et al., 1993. *J. Invest. Dermatol.* 105: 14–21; Rochat, et al., 1994. *Cell* 76: 1073–1076; Moll, 1995. *J. Invest. Dermatol.* 105: 14–21. Additionally, human ORS cells which are isolated from plucked anagen scalp hair follicles can be expanded extensively in vitro. See e.g., Weterings, et al., 1981. *Brit. J. Dermatol.* 104: 1–5; Limat and Noser, 1986. *J. Invest. Dermatol.* 87: 485–488; Imcke, et al., 1987. *J. Am. Acad. Dermatol.* 17: 779–786; Limat, et al., 1989. *J. Invest. Dermatol.* 92: 758–762. Under conventional submerged culture conditions, ORS cells resemble interfollicular epidermal keratinocytes by both morphologic and biochemical (e.g., keratin profiles) criteria. See e.g., Stark, et al., 1987. *Differentiation* 35: 236–248; Limat, et al., 1989. *J. Invest. Dermatol.* 92: 758–762; Limat, et al., 1991. *Ann. N.Y. Acad. Sci.* 642: 125–147. In organotypic co-cultures with human dermal fibroblasts (i.e., under conditions mimicking the epidermal environment), ORS cells with respect to histological, immunohistological, ultrastructural and biochemical criteria develop a stratified epithelium reminiscent of regenerating epidermis. See e.g., Lenoir, et al., 1988. *Dev. Biol.* 130: 610–620; Limat, et al., 1991. *Exp. Cell Res.* 194: 218–227; Limat, et al., 1991. *Ann. N.Y. Acad. Sci.* 642: 125–147. If such organotypic cultures are grafted onto nude mice, ORS cells form a regular neo-epidermis that is under homeostatic control. See e.g., Limat, et al., 1995. *Transplantation* 59: 1032–1038. Thus, human ORS cells are of considerable interest for clinical application.

In the previous decade, interest has focused on the use of cultured epithelial cells for wound coverage. First, sheets of cultured autologous interfollicular keratinocytes were grafted successfully on acute wounds, mainly in the treatment of larger third degree burns (see e.g., O'Connor, et al., 1981. *Lancet* 1: 75–78; Compton, et al., 1989. *Lab. Invest.* 60: 600–612) but also of epidermolysis bullosa (see e.g., Carter, et al., 1987. *J. Am. Acad. Dermatol.* 17: 246–250), pyoderma gangrenosum (see e.g., Dean, et al., 1991. *Ann. Plast. Surg.* 26: 194–195; Limova and Mauro, 1994. *J. Dermatol. Surg. Oncol.* 20: 833–836), and wounds after excision of giant congenital nevi (see e.g., Gallico, et al., 1989. *J. Plast. Reconstr. Surg.* 84: 1–9) or separation of conjoined twins (see e.g., Higgins, et al., 1994. *J. Royal Soc. Med.* ??:108–109).

In contrast to the treatment of such acute wounds, the grafting of chronic wounds (e.g., leg ulcers) with cultured keratinocytes has been much less successful. Allografts do not result in a permanent "take" (see e.g., Fabre, 1991. *Immunol. Lett.* 29: 161–166) and thus may be classified as a " . . . quite effective but expensive biological dressing". See Phillips, et al., 1989. *J Am. Acad. Dermatol.* 21: 191–199. A reproducible, major definite "take" of autologous keratinocyte grafted by various modalities including: sheets of submerged keratinocyte cultures consisting of only a few, noncornified cell layers (Hetton, et al., 1986. *J. Am. Acad. Dermatol.* 14: 399–405; Leigh and Purkis, 1986. *Clin. Exp. Dermatol.* 11: 650–652; Leigh, et al., 1987. *Brit. J. Dermatol.* 117: 591–597; Harris, et al., 1993. *Clin. Exp. Dermatol.* 18: 417–420), trypsinized single cells attached to collagen-coated dressings (Brysk, et al., 1991. *J. Am. Acad. Dermatol.* 25: 238–244), skin equivalents (Mol, et al., 1991. *J. Am. Acad. Dermatol.* 24: 77–82, 1991) has yet to be convincingly documented within the scientific literature. The same lack of quantitative findings also holds true for various reports on the grafting of freshly isolated, autologous interfollicular keratinocytes (Hunyadi, et al., 1988. *J. Dermatol. Surg. Oncol.* 14: 75–78) or ORS cells (Moll, et al., 1995. *Hautarzt* 46: 548–552) fixed to the wound bed by the use of a fibrin glue. However, it should be noted that the disadvantages of the bovine serum used during cultivation of the keratinocytes may contribute to reduced "take" rate, due to the fact that it resists in keratinocytes. See e.g., Johnson, et al., 1990. *J. Burn Care Rehab.* 11: 504–509.

SUMMARY OF THE INVENTION

Prior to the disclosure of the present invention herein, the standard methodology for the generation of a primary culture of basal keratinocytes consisted of the plucking of an anagenic (i.e., growing hair shaft) hair followed by a careful microscopic dissection to remove the hair bulbs and the infundibular hair shaft. The resulting outer root sheath (ORS) was then placed on the culture insert for initiation of the primary keratinocyte culture. However, numerous subsequent studies (approximately 200), wherein the anagenic hair was placed directly on the culture insert without performing the initial micro-dissection to remove the hair bulbs and the infundibular hair shaft, have demonstrated that such tedious and time-consuming dissection of the plucked anagenic hair was not required. This has served to markedly simplify the handling process, reduce the risk for contamination, and resulted in more efficient initiation of keratinocyte cell plating.

Accordingly, it is an object of the present invention to provide improved and simplified methods for the generation of keratinocytes or keratinocyte precursors from outer root sheath cells (ORS cells) in fully defined culture conditions for the treatment of various types of skin defects (e.g., chronic wounds such as leg ulcers, diabetic ulcers, pressure sores, and the like) in both humans and animals. In addition to their use in the treatment of wounds, keratinocytes may also be used in plastic and cosmetic surgery, or whenever there is a demand for such skin support (e.g., post operative following the removal of tattoos, naevi, skin cancer, papillomas, after amputation, in sex transformation or re-virgination, and the like).

These aforementioned objectives are accomplished by explantation and culture of plucked, anagenic or growing hairs in toto upon microporous membranes carrying human fibroblast feeder cells at their under-surface. In such primary cultures, large numbers of ORS cells can be easily and repeatedly obtained, irrespective of the donor's chronological age. Such ORS cells may be used for the subsequent preparation of dermal or epidermal equivalents or kept frozen and stored in order to use them at a later time point.

The subsequent preparation of dermal or epidermal equivalents is achieved by the "seeding" of these ORS cells upon a modified, microporous membranes carrying fibroblast feeder cells (most preferably growth-arrested/limited human fibroblast "feeder cells") at their under-surface. During culture, these ORS cells undergo tissue differentiation which has been demonstrated to be similar to that of normal epidermis. This finding is most probably due to a large compartment of proliferating cells. The modified culture conditions which are disclosed herein are important for the successful treatment of chronic wounds with epidermal equivalents generated in vitro from autologous ORS cells.

A further object of the present invention to provide improve culture systems for ORS-derived keratinocytes by adhering the anagenic hair onto a polymeric microporous membrane coated with one or more molecules of extracellular matrix origin. These improved cultures of ORS cells, designated as dermal equivalents or epidermal equivalents, may be used to treat skin defects, especially chronic wounds.

Yet another object of the present invention to produce dermal or epidermal equivalents using a reduced concentration of allogenic or homologous serum. This greatly mitigates the risk of disease transmission, for example, by clinical use of blood products, by the use of autologous or homologous human serum and substances derived or released from blood components (e.g., blood platelets) for supplements in in vitro culturing steps.

A further object of the present invention is a methodology which ameliorates the probability of mechanical damage (e.g., separation of the various constituent layers) of the dermal or epidermal equivalents during transport prior to transplantation.

The clinical advantages of the methodology of the present invention, as compared to grafting techniques of chronic wounds which have been previously utilized, include, but are not limited to: noninvasiveness (so that the cells are available repeatedly), the lack of need for surgical facilities or anesthesia during the grafting procedure, and a short immobilization period of only 2 hours is required following the grafting procedure.

DETAILED DESCRIPTION OF THE INVENTION

Unless defined otherwise, all technical and scientific terms used herein have the same meanings commonly understood by one of ordinary skill in the art to which this invention belongs. Although any methods and materials similar or equivalent to those described herein can be used in the practice of the present invention, the preferred methods and materials are now described. All publications mentioned herein are incorporated herein in their entirety by reference.

The term "keratinocyte layer" as used herein means an in vitro generated keratinocyte tissue culture with more or less differentiated structure. The term "epidermal equivalent" as used herein means an in vitro generated organotypic tissue culture resembling in its histological structure the natural epidermis especially concerning the stratification and development of the horny layer. A normal stratified epidermis consists of a basal layer of small cuboidal cells, several spinous layers of progressively flattened cells, a prominent granular layer and an orthokeratotic horny layer. All these layers can be detected in the epidermal equivalents that are subject of the invention. Localization of those epidermal differentiation products that have been assayed by immunohistochemistry (e.g. keratin, involucrin, filaggrin, integrins) is identical to that found in normal epidermis.

The term "autologous" as used herein means: (i) that biological material is derived from the individual to be treated with epidermal equivalents; or (ii) that biological material added to tissue cultures comes from the donor of the cells for tissue culture.

The term "homologous" as used herein means: (i) that biological material is derived from one or more individuals of the same species as the individual to be treated with epidermal equivalents; or (ii) that biological material added to tissue cultures comes from one or more individuals of the same species as the donor of cells for the tissue culture.

The term "organotypic culture" and the like, refers to culture of cells under conditions that promote differentiation of the cells. Under conditions of organotypic culture, proliferation of the cells is slowed compared to culture under "proliferative" conditions such as primary culture conditions, and may be completely stopped. In the present case, an important condition for organotypic culture is maintenance of the cells at the air-liquid interface, a so-called "lifted" culturing condition.

The term "releasate from blood components" (e.g., blood platelets) as used herein means any combination of cytokines or other growth factors obtained from blood components (e.g., blood platelets). Platelets stimulated with, for example, thrombin release the content of their alpha granules into the surrounding medium. Alpha granules usually contain several cytokines (e.g., platelet derived growth factor (PDGF), epidermal growth factor (EGF), transforming growth factors alpha and beta (TGF alpha/beta), platelet factor 4 (PF-4), platelet basic protein (PBP)). However, it is possible to obtain cytokines and other growth factors from platelets by other methods than stimulating with thrombin. Moreover, other blood components produce growth factors and cytokines as well. Monocytes, for example, produce IL-1, TNF alpha, IL-6 and other substances of interest; whereas lymphocytes produce, for example, keratinocyte growth factor (KGF).

General Method for Preparing Epidermal Equivalents from ORS Cells

Keratinocyte precursor cells are selected from outer root sheath (ORS) of anagenic or growing hair which is derived from the individual which is to be subsequently treated with epidermal equivalents. In general, approximately 40 hair follicles are plucked from the scalp, and those in the anagenic phase (i.e., a growing hair shaft) are then selected under the dissecting microscope. A total of four weeks of culture is usually required in order to obtain approximately 1 cm² of epidermal equivalents from the five hair follicles. However, with improved culture and fermentation techniques it may be possible to get a higher yield (i.e., a larger area of epidermal equivalents, within this period of time).

It should be noted that the previous, standard method for the generation of a primary culture of basal keratinocytes consisted of the plucking of an anagenic (i.e., growing hair shaft) hair followed by a careful microscopic dissection to remove the hair bulbs and the infundibular hair shaft. The resulting outer root sheath (ORS) was then placed on the culture insert for initiation of the primary keratinocyte culture. However, numerous subsequent studies (approximately 200), wherein the anagenic hair was placed directly on the culture insert without performing the initial micro-dissection to remove the hair bulbs and the infundibular hair shaft, have demonstrated that such tedious and time-consuming dissection of the plucked anagenic hair was not required. This has served to markedly simplify the handling process, reduce the risk for contamination, and resulted in more efficient initiation of keratinocyte cell plating.

The selected anagenic hairs were incubated in an appropriate rinsing buffer containing various anti-microbial and anti-fungal agents (e.g., fungizone, penicillin, and streptomycin). Following this procedure, the entire plucked anagenic hair is placed directly on the culture insert and allowed to grow for several days, preferably 7–14, days, and more preferably 8 to 10 days. An optional, additional step is comprised of passaging the primary culture and performing a secondary culture in order to obtain more cellular material for the preparation of larger areas of epidermal equivalents.

Primary dermal fibroblasts are plated on the underside of a culture insert which is comprised of a microporous membrane which is coated with one or more extracellular matrix substances (e.g., fibrin, fibronectin, collagens, laminins or hyaluronan or mixtures thereof) that carries a growth-arrested/limited feeder cell system on its undersurface. The coating of the membrane insert with such extracellular matrix substances provides for: (i) an enhanced culture surface for the initial attachment of the anagenic hair (i.e., it sticks easily and remains stationary); (ii) a surface which significantly enhances the migration of the basal keratinocytes away from the outer root sheath (ORS) anagen hair follicles; and (iii) increased growth rates of the spreading basal keratinocytes (i.e., the overall culture time needed for production of fully differentiated skin equivalent (EpiGraft™) can be reduced to three weeks, instead of four.

The aforementioned growth-arrested/limited feeder cell system located on the under of the microporous membrane insert is comprised of primary dermal fibroblast obtained from a human epidermal skin biopsy. The primary dermal fibroblasts are then plated on the underside of the culture insert and treated with mitomycin-C for 24 hours prior to their use as a "feeder cell layer" for the plucked anagen hair. Growth arrest/limitation is induced by either mitomycin-C or X-ray treatment or, preferably, the reduced of serum concentration below 5%, and preferably 2%. It should be noted that, although some cultures had been performed using 10% fetal calf serum (FCS; Boehringer Mannheim, Germany), the current utilization of human serum, in order to reduce the number of allogeneic ingredients, was found to provide markedly superior outgrowth and proliferation of the ORS cells. Moreover, the human serum is preferably utilized in a concentration of less than 5%, and more preferably in a concentration of 2%. In the presence of such low serum concentrations, the primary human dermal fibroblasts of the present invention will become significantly, or completely growth arrested. Hence, in this manner, two expensive and potentially complicating steps in the autologous hair root culture system may be removed. The two complicating steps include: (i) removal of high serum >5% concentrations, which reduces the overall cost of the process significantly and; (ii) the removal of mitomycin-C treatment, which provides a fully mitomycin-C-free culture system and eliminates any concerns regarding the total elimination of the drug from the primary culture inserts prior to the growth of the Epigraft™ cultures. In addition, the use of reduced of serum concentrations allows the alternative feeder cell-arresting procedure (i.e., the X-ray exposure step) to be eliminated, thus saving significant time and expense in the overall procedure.

Following expansion of the ORS cells to an appropriate density (i.e., $1 \times 10^3$ to $1 \times 10^6$ cells/cm², and preferably $5 \times 10^4$ to $1 \times 10^5$ cells/cm²), they are used for preparation of epidermal equivalents. Preferably, the cells are grown to confluence. The epidermal equivalents are prepared by seeding ORS cells at an appropriate cell density (i.e., $30 \times 10^3$ to $100 \times 10^3$ cells/cm², and preferably $60 \times 10^3$ cells/cm²) within a culture device which is suitable for "lifting" the cells up to the air-liquid interface during culture. Subsequently, one-half to three days after seeding (preferably 1 day after seeding), the ORS cells are exposed to air (e.g., by aspiration of the medium inside the insert) and the cultures are then continued for approximately 10–20 days, and preferably for 14–18 days, in such "lifted" culture condition. The medium is changed periodically during the lifted cultured; preferably every two to four days, and most preferably every three days.

The present invention also encompasses dermal equivalents which include additional layers, and so are more complex structures than epidermal equivalents. Dermal equivalents comprise differentiated ORS cells as their epidermal part and also a layer comprising a matrix component, preferably one containing embedded dermal fibroblasts and/or other cells (i.e., an "embedding matrix"). Dermal equivalents are made by placing a matrix with one or more extracellular matrix substances (e.g., fibrin, fibronectin, collagens, laminins or hyaluronan or mixtures thereof) on the upper surface of the microporous membrane described above. When embedding human dermal fibroblasts, preferably autologous human dermal fibroblasts, the cells are embedded at a density of $1 \times 10^3$ to $1 \times 10^7$ cells/cm²; preferably $1 \times 10^4$ to $1 \times 10^5$ cells per cm²; and most preferably approximately $5 \times 10^4$ cells/cm². The primary culture of ORS cells is then seeded on top of the matrix (preferably containing embedded dermal fibroblasts and/or other cells) and organotypic culturing is performed as described above. For a detailed description of the preparation of dermal equivalents, see e.g., Limat, et al., 1991. *Exp. Cell Res*. 194: 218–277.

It should be noted, however, that the cells which are embedded in the matrix need not be limited exclusively to dermal fibroblasts; as epidermal, mesenchymal, neuronal and/or epithelial cells can also be utilized. The embedded cells are preferably obtained from skin tissue, are more preferably allogeneic cells, and are most preferably autologous cells.

All culture steps are performed in an appropriate medium which allows the proliferation of the ORS cells and their outgrowth from the hair follicles, the medium is typically changed every 2–5 days, and preferably every 3 days. Generally, the medium utilized for all steps is the same. The medium is typically based on a minimal medium and contains several additional ingredients. One common ingredient is serum in a concentration of 0.5–60%. In the preferred embodiment of the present invention, human serum is used at a concentration of less than 5%, and most preferably at a concentration of 2%. Furthermore, with the development of serum-free media, it may be possible to omit serum in toto. Epidermal growth factor (EGF) stimulates migration of keratinocytes and delays their senescence which results in stimulation of proliferation. Cholera toxin, hydrocortisone, insulin, adenine and trijodothyronine have an effect of stimulating proliferation. All of these ingredients are thus useful in a medium for preparing epidermal equivalents. Nevertheless, it may be possible to omit or replace one or another of these ingredients.

Releasate from blood components (e.g., blood platelets, monocytes or lymphocytes), may serve as a source of cell proliferating activities, and therefore may substitute serum and provide other above mentioned ingredients. For certain culture periods the serum-containing medium might possibly be replaced by a defined, serum-free medium, for example, SFM (Gibco Europe, Ettlingen). The releasate from blood components (e.g., blood platelets, monocytes or lymphocytes), especially of homologous or autologous origin, may serve as a source of cell proliferating activities and therefore may substitute serum and provide other above mentioned ingredients or indeed may provide additional ingredients. The blood components should be added to the culture medium in a concentration of 0.1% to 20%, and preferably 1% to 5%, after the releasate is brought-to the same final volume as the blood from which these components are obtained. These releasates contain several growth factors that are present in serum (e.g., PDGF, ECF or TGFs). However, serum as well as releasates contain many substances, and not all are characterized.

Releasate from blood platelets is obtained by centrifugation of anti-coagulated whole blood, preferably human blood, in order to pellet all cells except thrombocytes. The supernatant is centrifuged once more to spin down the thrombocytes. The thrombocytes are suspended in an appropriate buffer, e.g. phosphate buffer and treated with thrombin in order to release their alpha granules which contain a mixture of various growth factors (e.g., PDGF, PF-4, TGF-β, EGE, β-thromboglobulin. In a further centrifugation step all cellular material is removed. Finally, the supernatant is supplemented with buffer to the volume of the original blood sample from which the components are obtained. The blood components should be added to the culture medium in a concentration of 0.1% to 20%; preferably 1% to 10%; and more preferably 2 to 5%.

Similarly, releasates can be obtained from other blood cells, such as monocytes, by breaking up the cells (e.g., by sonication, freeze-thaw method, or the like) and purifying the growth factors (e.g., by filtration or immunological methods).

The blood component releasates can also be used to condition the wound bed in the course of grafting the epidermal or dermal equivalents. Furthermore, the culture medium containing the releasates and used to perform the organotypic culturing step, after having been conditioned by the cells, can be used to condition the bed of the skin defect in the course of grafting the epidermal or dermal equivalents.

Cultivation usually is performed in inserts with microporous membranes, which contain homologous or autologous dermal fibroblasts (HDF), especially postmitotic HDF at their undersurface. HDF secrete factors that condition the medium in order to get a better growth of the epidermal equivalents. The HDF layer can be formed from between $5 \times 10^3$ to $1 \times 10^5$ cells, and preferably approximately $1 \times 10^4$ to $5 \times 10^4$ cells. The HDF are preferably postmitotic, but earlier passage cells can be used if they are irradiated, treated with mitomycin-C, or otherwise treated to inhibit their proliferation but maintain their metabolism.

Microporous membranes are suitable as a culture substrate, because they allow substances to diffuse from one side to the other, but work as a barrier for cells. The pore size of the membrane is not a limitation on the present invention, but should be adequate so as to allow diffusion of proteins of up to 100,000 Daltons molecular weight, and preferably of up to 70,000 Daltons molecular weight. The membrane should at least allow diffusion of small hormones such as insulin, and allow passage of proteins of up to 15,000 Daltons molecular weight. Other means than a microporous membrane for performing the function of allowing diffusion of soluble factors to the cultured ORS cells, while preventing mixing of the ORS cells with the HDF would also be usable.

The microporous membranes typical in the art are usually used. However, membranes fabricated from a biodegradable material (e.g., polyhyaluronic acid or polylactic acid) can also be used. When a biodegradable microporous membrane is employed it is contemplated that the entire culture, including the differentiated ORS cells, the microporous membrane and the MDF, will be transplanted into the skin defect. Thus, in this alternative embodiment, the HDF grown on the underside of the membrane need not be post-mitotic or treated to preclude proliferation. While HDF tend to be less immunogenic than keratinocytes, it is preferable that when this embodiment is employed, the HDF be allogeneic cells, preferably autologous cells.

The epidermal equivalents of the present invention may range in size from approximately 6 mm to approximately 2.5 cm in diameter, with a preferred diameter of 2.5 cm. For practical reasons, the experiments disclosed herein were performed with epidermal equivalents of approximately 2.5 cm in diameter. Further clinical treatments will be performed so as to ascertain whether this size is generally applicable, or if other sizes will be more convenient for use in some cases.

In many cases, however, the epidermal equivalents will have to be delivered from the facility where they are generated to the institution where they are used. Therefore a system is needed to enable the transport of the epidermal equivalents. Hence, the technique of placing the epidermal equivalents onto a carrier (e.g., a polyester membrane) and preferably adhering them to the carrier was developed. As an adhesive, fibrin glue is preferred, however, other options, including, but not limited to: extracellular matrix components such as collagen, fibronectin, proteoglycans (e.g., hyaluronic acid, chondroitin sulfate, and the like), or basement membrane zone components (e.g., laminin, Matrigel™, or L-polylysine), or similar tissue glues, may also be utilized. The epidermal equivalents are preferably adhered to the carrier with their top, cornified layer in contact with the carrier.

The carrier utilized in the present invention may consist of a synthetic membrane, made from at one or more of the following materials (polyester, PTFE or polyurethane); from one or more biodegradable polymers (e.g., hyaluronic acid, polylactic acid or collagen); or a silicone or vaseline gauze dressing, or any other material suitable for wound dressing. These materials which are suitable for wound dressing allow the carrier to remain in place to immobilize the implanted dermal or epidermal equivalents for several days, rather than requiring the carrier to be removed immediately after the dermal or epidermal equivalents are transplanted.

The dermal or epidermal equivalents put onto the carrier have to be kept in a condition ready for grafting. Irrespective of whether the microporous membrane is removed from the basal cell layer for transport, conditions resembling those during cultivation seem to be favorable. In order to keep the dermal or epidermal equivalents in contact with medium only from the basal layer (i.e., during cultivation), agarose in a concentration ranging from 1% to 5%, and preferably in a concentration of 1 to 3%; methyl cellulose; or any other gelifying substance in comparable concentrations, may be used to solidify the medium. The epidermal equivalents together with the carrier will be placed with their basal layer on top of the solidified or gelled medium. The whole device is then sealed in an air tight manner, and shipped. The epidermal equivalents are, most preferably, used for grafting within 24 hours of initial packaging.

The dermal or epidermal equivalents are transplanted by simply placing them in the bed of the wound or other skin defect. Preferably the dermal or epidermal equivalents are then immobilized (i.e., preferably for at least 2 hours). The preferred method for immobilization is by use of a biodegradable material, by some sort of tissue glue or a bandage such as described above for the transport carrier material. As previously described, the bed of the skin defect can be treated with blood releasates or the medium from the organotypic culturing prior to, or concomitantly with the transplantation.

2. Specific Examples

A. Preparation of ORS Cells

Keratinocyte precursor cells from the outer root sheath (ORS) of the hair follicles are selected and subsequently cultured by use of the following methodology, as disclosed in the present invention.

Approximately 40 hair follicles were plucked with tweezers from the occipital scalp of individuals, and those in the anagen phase, as detected, for example, by well-developed root sheaths, were then selected under the dissecting microscope. See e.g., Limat and Noser, 1986. *J. Invest. Dermatol.* 87: 485–488; Limat, et al., 1989. *J. Invest. Dermatol.* 92: 758–762. As previously discussed, the anagen hair was placed directly on the microporous culture insert without performing the previously-utilized micro-dissection to remove the hair bulbs and the infundibular hair shaft.

Generally, six anagenic hairs were explanted on the microporous membrane of a cell culture insert (Costar) that carried on its undersurface a preformed feeder layer preferably comprised of $20 \times 10^3$ postmitotic human dermal fibroblasts (HDF) per $cm^2$. See e.g., Limat, et al., 1989. *J. Invest. Dermatol.* 92: 758–762. The HDFs were derived from skin explants of a healthy, repeatedly HIV- and hepatitis-serology negative individuals and cultured in DMEM supplemented with 10% fetal calf serum (FCS), or preferably less than 5% human serum, or most preferably 2% human serum.

For the purpose of obtaining an efficient outgrowth of the outer root sheath (ORS) cells from the anagenic hair and a high proliferation rate, it is important not to place the HDF feeder cells at the bottom of the culture dish, resulting in an additional medium layer between the HDF layer and the microporous membrane supporting the ORS cells. Growing each cell type at one side of the microporous membrane allows a very close interaction, but prevents cross contamination of the ORS cells with fibroblasts and thus guarantees a pure culture of ORS cells.

The culture medium which was utilized consisted of Dulbecco's modified Eagle's medium/F12 (3:1 v/v) supplemented with 2% human serum, 10 ng of epidermal growth factor per ml of culture medium, 0.4 microgram of hydrocortisone per ml, 0.135 mM adenine, and 2 nM triiodothyronine (all obtained from Sigma Chemical Co., St. Louis, Mo.). The preferred final $Ca^{2+}$ concentration of the culture medium is 1.5 nM (see e.g., Wu, et al., 1982. *Cell* 31: 693–703; Limat and Noser, 1986. *J. Invest. Dermatol.* 87: 485–488). Within about 2 weeks, the ORS cells had expanded and reached confluence. They were dissociated with 0.1% trypsin/0.02% EDTA mixture, checked for viability, and used for preparation of epidermal equivalents. It should be noted that, although initial cultures had been performed using 10% fetal calf serum (FCS; Boehringer Mannheim, Germany), current utilization of human serum, in order to reduce the number of allogeneic ingredients, provided superior outgrowth and proliferation of the ORS cells. The human serum is preferably utilized in a concentration of less than 5%, and most preferably in a concentration of 2%.

Explanting plucked anagen hairs directly on the membrane of culture inserts carrying postmitotic HDF on the undersurface as feeder cells proved to be a simple, efficient, and reproducible method for establishing primary cultures of ORS cells. Approximately 80% of the explanted hair follicles gave rise to outgrowth of ORS cells, even when derived from individuals aged up to 91 years. After 14 days, large areas of the insert were covered by compactly arranged small cells, at which time they were used for preparation of epidermal equivalents of the present invention.

The comparison of the growth behavior of 70 strains of ORS cells, which were derived from a total of 30 donors, demonstrated no significant differences between the young (i.e., 21 donors aged 19–50 years) and the old (i.e., 9 donors aged 51–93 years) donors. Approximately $5 \times 10^5$ cells were generally obtained per explanted follicle and the overall degree of cell viability was typically higher than 95%. In contrast, in the absence of postmitotic HDF as a feeder layer, there was only sporadic outgrowth of ORS cells from the explanted follicles.

B. Preparation of Epidermal Equivalents

ORS cells harvested from primary cultures were seeded at a density of $30 \times 10^3$ cells/$cm^2$ to $100 \times 10^3$ cells/$cm^2$, and preferably $60 \times 10^3$ cells/$cm^2$, on cell culture inserts (Falcon 3095) which had been previously inoculated with $10 \times 10^3$ cells/$cm^2$ to $50 \times 10^3$ cells/$cm^2$, and preferably $20 \times 10^3$ cells/$cm^2$, of postmitotic HDF cells on the undersurface of their microporous membrane. Similar to the culture of ORS cells, it is important to keep the HDF feeder cells in close proximity with the ORS cells, while concomitantly keeping them separated by use of the microporous membrane. This culture technique enhances proliferation, differentiation, and thus the homeostasis of the developing tissue.

Culture medium was identical that that utilized for the preparation of the primary cultures as described supra. After 24 hours, the ORS cells were exposed to air by aspiration of the liquid medium inside the insert (i.e., leaving the underside of the insert in contact with medium) and cultured for an additional 12–14 days, with three medium changes per week.

For transplantation, the epidermal equivalents were excised from the insert together with the underlying microporous membrane by means of a 2.5 cm punch (Stiefel Laboratorium) and positioned in an upside-down orientation upon a pre-punched polyester membrane (Thomapor 95877®; Reichelt Chemie, Heidelberg, Germany) of an equivalent diameter (i.e., 2.5 cm). The insert membrane, together with the attached postmitotic HDF, was then carefully removed by means of fine tweezers, thus avoiding the previously-required enzymatic treatment. The use of this polyester membrane not only serves as transfer membrane, but also preventing the shrinking or rolling-up of these relatively large epidermal equivalents by adhesion. The epidermal equivalents, and their supporting polyester membranes, were then washed in Dulbecco's phosphate-buffered saline (PBS) and left floating thereon until their subsequent application on the wound bed (i.e., generally for no longer than 30 minutes).

In contrast to the methodology of the present invention, the currently-utilized protocol, which is generally employed for preparation of the fully differentiated epidermal equivalent for wound grafting, requires the phycisian to carefully cut the entire perimeter of the culture insert with a scaple blade so as to facillitate the release of the insert membrane (with undercoated human dermal fibroblasts) with the attached skin patch squamous-side up. The skin patch is then released from this membrane by peeling with a fine forceps and placed, basal-side up, on a new membrane disk in a culture dish for eventual transplant to the patient. This aforementioned procedure is both laborious and time consumming, and can lead to reversal of the basal and squamous orientation.

A markedly simpler method has been devised which utilizes a membrane patch cap (analogous to the fibrin glue patch procedure described below) which is placed directly on top of the squamous surface layer. The membrane cap can then be easily grasped together with the skin patch below using fine forceps and peeled from the culture insert well surface. The membrane cap the serves a plate for placing the graft onto the wound without mixing up the orientation of the graft (i.e., basal side down, squamous side up).

For stabilization and as a protective coating in case of grafting, the epidermal equivalents of the present invention are coated on top with diluted fibrin glue, which also serves to clearly identify the upper (i.e., cornified) side. Fibrin glue, the preferred embodiment of the present invention, is a generally-accepted, natural human product which is used extensively as a tissue glue. By applying a thin coating of fibrin glue (which is clearly visible with the naked eye) to the cornified squamous air-exposed surface of the epidermal skin equivalent, the physician placing the epidermal skin equivalent onto the wound site will be fully assured of proper graft orrientation (i.e., the basal surface of the skin patch will always be the side that does not have the clearly visisble fibrin glue cap). Previously, in many instances, during the preparation of the epidermal patch for wound grafting, the orientation of the patch becomes confused. Should the skin patch be placed in squamous-side down orrientation onto the graft site, there would be significantly decreased likelihood of a succesful graft. Thus, the use of this simple "marking" completely eliminates this problem.

In addition, anti-microbial and/or anti-fungal substances may also be included in the fibrin glue, so as to impede any possible microbial contamination or overgrowth of the graft. Many chronic lesions are chronically-infected, which can result in the inhibition of graft "take" and subsequent wound healing following the initial skin grafting. Moreover, the addition of one or more antibiotics or anti-fungal agents by direct emulsification within the fibrin glue surface cap, may provide a significant improvement in the delivery of sufficient quantities of anti-microbial agents to the transplant site.

It should be noted that the ORS cells which were harvested from primary cultures, and cultured at the air-liquid interface on insert membranes carrying postmitotic HDF at their undersurface, typically developed a stratified epithelium within 14 days. This stratified epithelium consisted of a basal layer of small cuboidal cells below a thick suprabasal compartment of progressively flattened cells. A prominent granular layer, as well as an orthokeratotic horny layer were also found to be present.

Based upon the experimental finding of approximately 80% of the follicles giving rise to ORB cell outgrowth, approximately five anagen hair follicles were required for the generation of 1 $cm^2$ of epidermal equivalents. The period to generate graftable epidermal equivalents usually was four weeks in toto (i.e., two weeks for the primary culture and two weeks for the subsequent organotypic culture).

EQUIVALENTS

From the foregoing detailed description of the specific embodiments of the present invention, it should be readily apparent that a unique methodology for the selection and culture of keratinocytes from the outer root sheath (ORS) of hair follicles for subsequent use in, for example, skin grafting procedures, has been described. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims. For example, the selection of anagen hairs are believed to be a matter of routine for a person of ordinary skill in the art with knowledge of the embodiments described herein.

What is claimed is:

1. A method for the treatment of a skin defect comprising
   (a) culturing an intact hair follicle of an anagenic hair to obtain outer root sheath cells;
   (b) culturing said outer root sheath cells in a medium containing human serum in a concentration of less than 5% to obtain keratinocyte precursor cells;
   (c) preparing an epidermnal or dermal equivalent comprising said keratinocyte precursor cells, wherein said keratinocyte precursor cells are seeded at a density of between $3 \times 10^4$ cells/$cm^2$ and $1 \times 10^5$ cells/$cm^2$; and
   (d) applying a portion of said epidermal or dermal equivalent to said defect.

2. The method of claim 1, wherein said outer root sheath cells are autologous cells obtained from an individual who will subsequently undergo treatment for a skin defect.

3. The method of claim 1, wherein said outer root sheath cells are homologous cells.

4. The method of claim 1, wherein said epidermal or dermal equivalent comprises outer root sheath cells cultured in a medium containing only homologous or autologous biological supplements.

5. The method of claim 1, wherein said epidermal or dermal equivalent is coated on its top or cornified side with a fibrin glue.

6. The method of claims 1 or 5, wherein said epidermal or dermal equivalent is coated on its top or cornified side with a fibrin glue which contains one or more anti-microbial, anti-fungal, or anti-viral agents emulsified therein.

7. A method for the treatment of a skin defect comprising
   (a) culturing an intact hair follicle of an anagenic hair to obtain outer root sheath cells;
   (b) culturing said outer root sheath cells to obtain keratinocyte precursor cells;

(c) preparing an epidermal or dermal equivalent comprising said keratinocyte precursor cells wherein said keratinocyte precursor cells are seeded at a density of between $3 \times 10^4$ cells/cm$^2$ and $1 \times 10^5$ cells/cm$^2$; and (d) applying a portion of said epidermal or dermal equivalent to said defect wherein all culturing of cells is performed in a medium which utilizes autologous or homologous human serum in a concentration of preferably less than approximately 5%.

8. The method of claim 7, wherein said outer root sheath cells are autologous cells obtained from an individual who will subsequently undergo treatment for a skin defect.

9. The method of claim 7, wherein said outer root sheath cells are homologous cells.

10. The method of claim 7, wherein said epidermal or dermal equivalent is coated on its top or cornified side with a fibrin glue.

11. The method of claim 7 or 10, wherein said epidermal or dermal equivalent is coated on its top or cornified side with a fibrin glue which contains one or more anti-microbial, anti-fungal, or anti-viral agents emulsified therein.

12. A method for the treatment of a skin defect comprising (a) culturing an intact hair follicle of an anagenic hair to obtain outer root sheath cells;

(b) culturing said outer root sheath cells in a medium containing human serum in a concentration of less than 5% to obtain keratinocyte precursor cells;

(c) preparing an epidermal or dermal equivalent comprising said keratinocyte precursor cells wherein said keratinocyte precursor cells are seeded at a density of between $3 \times 10^4$ cells/cm$^2$ and $1 \times 10^5$ cells/cm$^2$; and (d) applying a portion of said epidermal or dermal equivalent to said defect wherein said epidermal or dermal equivalent is coated on its top or cornified side with a fibrin glue.

13. The method of claim 12, wherein said outer root sheath cells are autologous cells obtained from an individual who will subsequently undergo treatment for a skin defect.

14. The method of claim 12, wherein said outer root sheath cells are homologous cells.

15. The method of claim 12, wherein said epidermal or dermal equivalent comprises outer root sheath cells cultured in a medium containing only homologous or autologous biological supplements.

16. The method of claim 12, wherein said epidermal or dermal equivalent is coated on its top or cornified side with a fibrin glue which contains one or more anti-microbial, anti-fungal, or anti-viral agents emulsified therein.

17. The method of claim 1, wherein the concentration of serum is less than 2%.

18. The method of claim 1, wherein the keratinocyte precursor cells are seeded at a density of $6 \times 10^4$ cells/cm$^2$.

19. The method of claim 7, wherein the concentration of serum is less than approximately 2%.

20. The method of claim 7, wherein the keratinocyte precursor cells are seeded at a density of $6 \times 10^4$ cells/cm$^2$.

21. The method of claim 12, wherein the concentration of serum is less than 2%.

22. The method of claim 12, wherein the keratinocyte precursor cells are seeded at a density of $6 \times 10^4$ cells/cm$^2$.

* * * * *